(12) United States Patent
Fike et al.

(10) Patent No.: US 9,410,118 B2
(45) Date of Patent: Aug. 9, 2016

(54) CELL CULTURE MEDIA AND METHODS

(71) Applicant: LIFE TECHNOLOGIES CORPORATION, Carlsbad, CA (US)

(72) Inventors: Richard Fike, Clarence, NY (US); Shawn Barrett, Clarence Center, NY (US); Zhou Jiang, East Amherst, NY (US); David Judd, Grand Island, NY (US)

(73) Assignee: Life Technologies Corporation, Carlsbad, CA (US)

( * ) Notice: Subject to any disclaimer, the term of this patent is extended or adjusted under 35 U.S.C. 154(b) by 75 days.

(21) Appl. No.: 14/367,413

(22) PCT Filed: Dec. 21, 2012

(86) PCT No.: PCT/US2012/071411
§ 371 (c)(1),
(2) Date: Jun. 20, 2014

(87) PCT Pub. No.: WO2013/096858
PCT Pub. Date: Jun. 27, 2013

(65) Prior Publication Data
US 2015/0064785 A1    Mar. 5, 2015

Related U.S. Application Data

(60) Provisional application No. 61/579,432, filed on Dec. 22, 2011.

(51) Int. Cl.
*B29C 67/24*    (2006.01)
*B29L 9/00*    (2006.01)
*C12N 5/00*    (2006.01)

(52) U.S. Cl.
CPC .............. *C12N 5/0018* (2013.01); *B29C 67/24* (2013.01); *C12N 5/005* (2013.01); *B29L 2009/00* (2013.01); *C12N 2500/30* (2013.01); *C12N 2511/00* (2013.01); *C12N 2533/40* (2013.01); *C12N 2533/74* (2013.01)

(58) Field of Classification Search
CPC ... A61K 2300/00; A61K 31/58; A61K 35/28; A61K 35/545; A61K 31/565; A61K 35/12; A61K 45/06; A61K 2800/782; A61K 31/00; A61K 8/63; A61K 38/39; A61K 8/14; A61K 8/65; A61K 9/0014; A61K 9/127; A61K 31/352; A61K 31/728; A61K 36/47; A61K 47/36; C08L 2666/22; C08L 69/00; C08L 85/02; C08L 101/00; C08L 57/08; C08L 67/02; C08L 2666/04; C08L 51/04; C08L 55/02; C08L 2666/02; C08L 2666/14; C08L 51/00; C08L 53/02; C08L 25/04; C08L 25/12; C08L 27/06; C08L 25/02; C08L 77/00; C08L 77/02; C08L 77/06; C08L 2666/08; B05D 2202/25; B05D 7/14; B05D 3/0254; B05D 1/00; B05D 1/22; B05D 2258/00; B05D 7/54; C22F 1/04; C22F 1/053; Y10T 428/2495; Y10T 428/31522; Y10T 428/31551; Y10T 428/31678; Y10T 428/265; B29C 67/24
See application file for complete search history.

(56) References Cited

FOREIGN PATENT DOCUMENTS

| WO | WO-03/005989 A2 | 1/2003 |
|---|---|---|
| WO | WO-03/086104 | 10/2003 |
| WO | WO-2004/060447 | 7/2004 |
| WO | WO-2007/094000 | 8/2007 |
| WO | WO-2011/049547 A1 | 4/2011 |
| WO | WO-2011/137274 A1 | 11/2011 |

OTHER PUBLICATIONS

Bhakay, A. et al., "Novel Aspects of Wet Milling for the Production of Microsuspensions and Nanosuspensions of Poorly Water-Soluble Drugs", *Drug Development and Industrial Pharmacy*, vol. 37, No. 8, 2011, 963-976.
PCT/US2012/071411, "International Search Report and Written Opinion mailed May 21, 2013", 11 Pgs.
PCT/US2012071411, "International Preliminary Report on Patentability mailed Jun. 24, 2014", 6 Pgs.

*Primary Examiner* — Debbie K Ware

(57) ABSTRACT

Compositions and methods are described for preparing media, feeds, and supplements. Such methods and medias may display increased stability of labile components and may use, for example, microsuspension and/or encapsulation technologies, chelation, and optionally, coating and/or mixing the labile compounds with anti-oxidants. The compositions may withstand thermal and/or irradiation treatment and have reduced virus number. These techniques may result in product with extended shelf-life, extended release of their internal components into culture, or in product that can be added aseptically into a bioreactor using minimal volumes. The compositions and methods may optimize the bioproduction workflow and increase efficiency.

20 Claims, 12 Drawing Sheets

Figure 1: New method for making micro/ nanosuspensions

Figure 2: Comparison of performance of microsuspensions and liquid feeds.

Figure 3: Schematic representation of an encapsulated microsuspension particle.

Figure 4: Impact of PLGA coating on delayed release of internal components from microcapsule or microsphere. a) top panel: no coating; b) bottom panel: comparison of coating with PLGA A and PLGA B.

Figure 5: Comparison of protein production in cells cultured with irradiated microsuspensions, or dry, encapsulated microsuspensions is similar to a control, liquid filter sterilized feed.

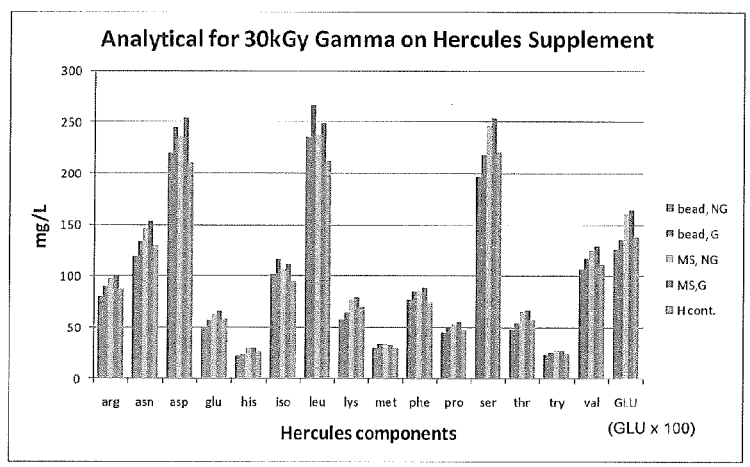
Figure 7: Negligible impact of gamma irradiation on microsuspensions or on dried, encapsulated microsuspensions

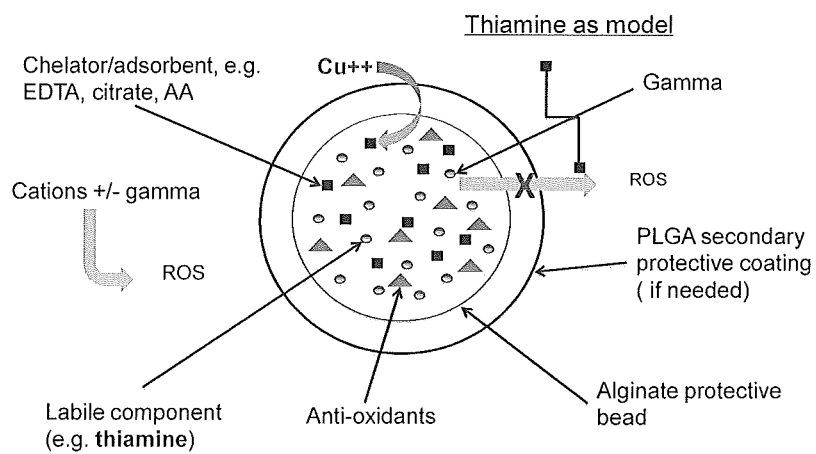
Figure 8 shows a schematic representation of a microencapsulated bead comprising a labile component.

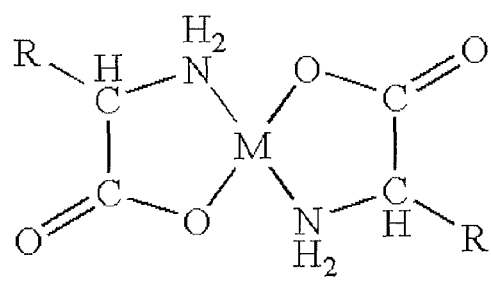
(a)
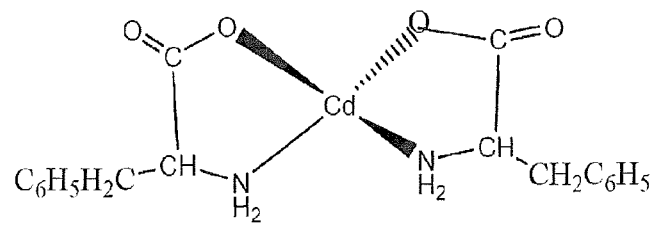
(b)
Figure 9: Chelation of reactive species: formation of exemplary coordinate complexes of metal ions in trace elements with amino acids.

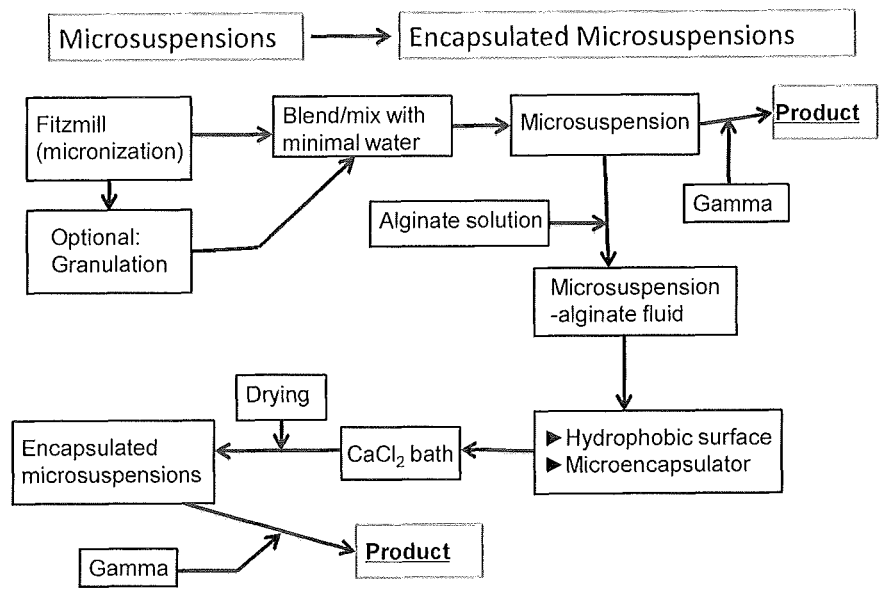
Figure 10: Schematic representation of methods of preparing microsuspensions and encapsulated microsuspensions.

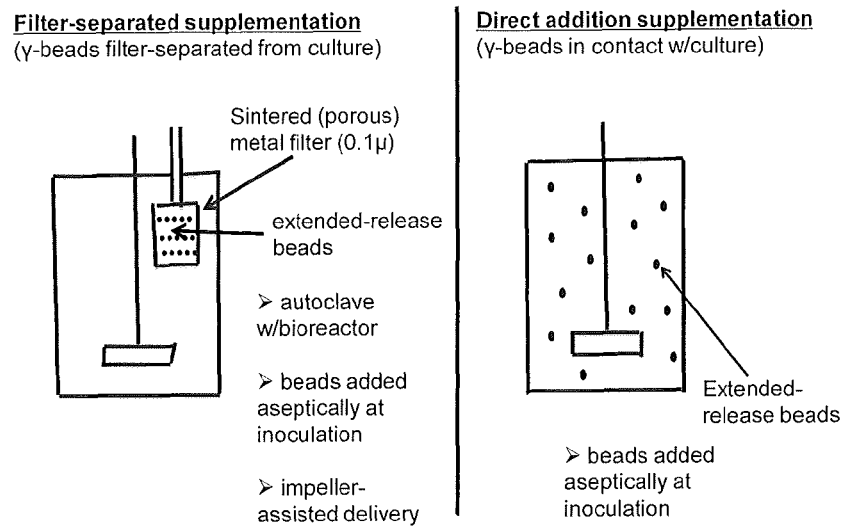
Figure 11: Two options for the direct addition of irradiated, microencapsulated beads to a bioreactor.

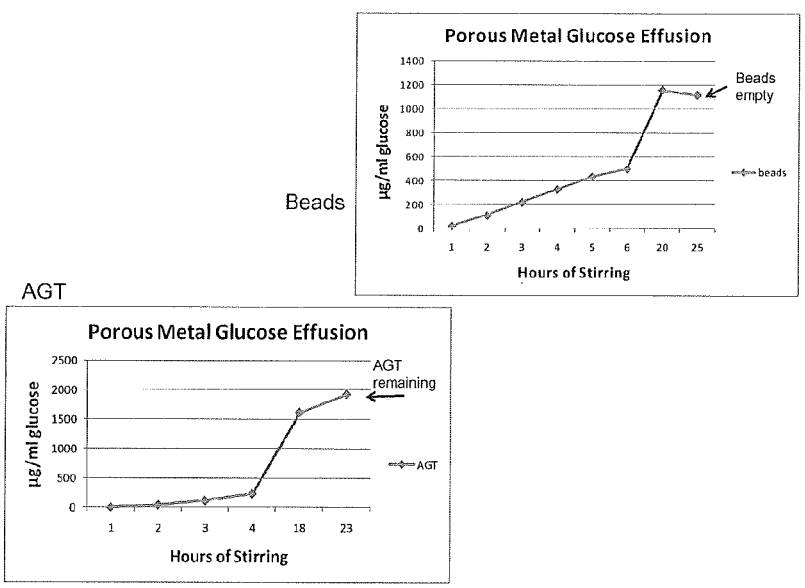
Figure 12: Comparison of extended release of supplement introduced into culture using the porous metal filter device for (a) microsuspension beads with PLGA coating: top panel, and (b) no beads, just AGT feed.

CELL CULTURE MEDIA AND METHODS

CROSS-REFERENCE TO RELATED APPLICATIONS

This application is a National Stage filing of PCT/US2012/071411, filed 21 Dec. 2012, which claims the benefit of U.S. provisional application no. 61/579,432, filed 22 Dec., 2011, under 35 U.S.C. §119(e), whose disclosures are herein incorporated by reference in their entirety.

TECHNICAL FIELD

Provided herein are compositions, methods and uses relating to novel types of cell culture media, feeds and supplements. The media, feeds and supplements have several desirable properties, which include but are not limited to, having certain components beyond their normal solubility limits, increased tolerance of radiation, extended release properties, high solubility, increased shelf life, and thermostability. Such characteristics, in certain embodiments, improve customer workflows and bioreactor productivity.

BRIEF DESCRIPTION OF THE FIGURES

The following figures, which are described below and which are incorporated in and constitute a part of the specification, illustrate exemplary embodiments that are not to be considered limiting to the scope of the disclosure.

FIG. 7 shows that there is negligible impact of gamma irradiation on microsuspensions, and on dried, encapsulated microsuspensions. This graph shows how encapsulated compounds (see far right) are impacted by 30 kGy of gamma being either in microcapsules ("bead") or as microsuspensions (MS) compared to non-irradiated liquid control. NG=no gamma irradiation, and G=gamma-irradiated.

FIG. 8 shows a schematic representation of a microencapsulated bead comprising a labile component, which is embedded and/or engulfed in anti-oxidants to protect the labile molecule, by reducing the impact of oxidation species generated during irradiation.

FIG. 9 shows chelation of reactive species and formation of exemplary coordinate complexes of metal ions in trace elements with amino acids.

FIG. 10 shows a schematic representation of methods of preparing microsuspensions and encapsulated microsuspensions.

FIG. 11 shows two options for the direct addition of irradiated, microencapsulated beads to a bioreactor. Left panel shows beads added within an autoclavable porous metal filter; or, right panel shows that beads can be added directly into the culture.

FIG. 12: Comparison of extended release of supplement introduced into culture using the porous metal filter device for (a) microsuspension beads with PLGA coating: top panel, and (b) no beads, just AGT feed.

SUMMARY OF THE DISCLOSURE

Figure 1:
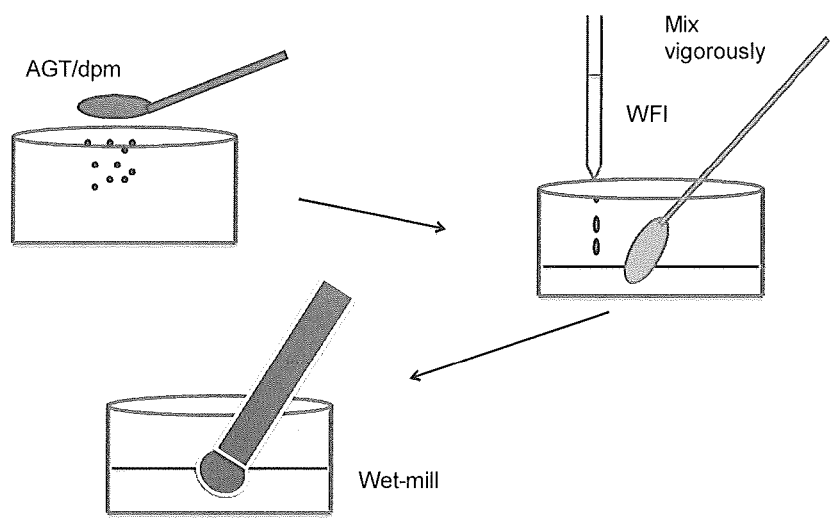
FIG. 1 shows a new procedure developed for making micro/nanosuspensions of cell culture media, feed and/or supplement components.
Figure 2:
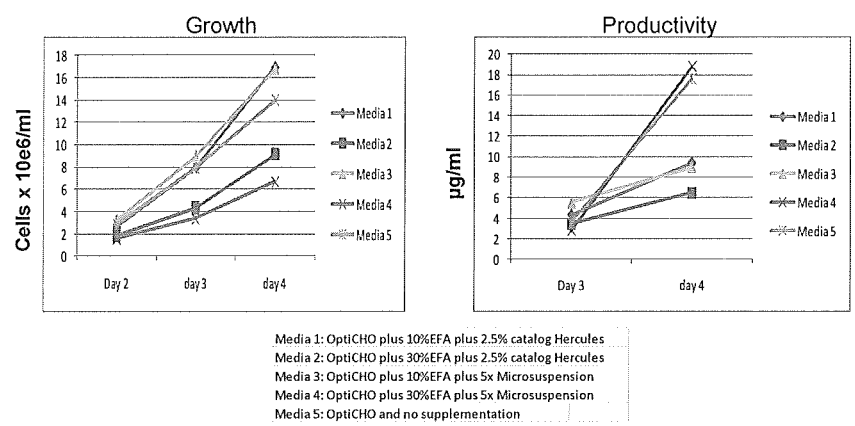
FIG. 2 shows a comparison of the performance of cell growth, protein production and delivery of microsuspensions and liquid feeds. Microsuspensions performed comparably to liquid feeds under the conditions tested and showed higher delivery efficacy than liquid feeds.

The media, feed and supplement compositions described in this disclosure have several desirable properties, which include but are not limited to, (i) ability to deliver certain components at "superconcentrated" levels extending far beyond their normal solubility limits in a culture system, (ii) increased ability to maintain media/feed functionality even after radiation sterilization, (iii) increased ability for extended release of internal components, (iv) high and quick solubility, (v) longer shelf life in dry format, (vi) increased thermostability, (vii) reduced risk of viral contamination up to 8 logs, (viii) the ability to be combined with other sterilizing technologies such as UV, filtration, and/or HTST pasteurization, (ix) the ability to be applied to a variety of media formats such as AGT, DPM, APM, as well as, to formulations having labile components at higher concentrations, (x) the ability to be applied to a variety of product types such as media, feeds, supplements, functional additives, etc. Due to these characteristics, the compositions can be added directly into a bioreactor or into a culture already in progress, and thereby can improve customer workflows and bioreactor productivity.

Accordingly, the compositions, methods and uses described in this disclosure are directed, in part, to cell culture media, concentrated feeds, functional additives, supplements that comprise a microsuspension; may also be directed to a novel cell culture media, feed and/or supplement composition comprising one or more encapsulated micro and/or nanosuspensions; and may further be directed to sterilizing the above compositions using radiation such that the functionality of the media/feed is maintained even after exposure to radiation. The present disclosure also provides methods of making such media, including characteristics of such media and its uses. Throughout this disclosure, some references may be made to cell culture media alone, but it would also include feeds and/or supplements, as applicable.

In one embodiment, the disclosure is directed to a method of making a media, feed or supplement composition, the method comprising: adding a minimal volume of an aqueous solution to a dry powder of the media, feed or supplement to make a paste; and mixing the paste vigorously to prepare a microsuspension.

In another embodiment, the disclosure is directed to a method of preparing a composition comprising a labile component comprising optionally, mixing in an effective amount of an anti-oxidant with the microsuspension of the labile component to form a mixture; encapsulating the microsuspension or the mixture of step 2 in a suitable capsular material such that a microcapsule or bead is formed; and drying the microcapsule or bead. In one embodiment, the labile substance is attached to a dendrimer. In any of these embodiments, the capsular material may be selected from the group comprising, for example, alginate, poly-L-lactic acid, chitosan, agarose, gelatin, hyaluronic acid, chondroitin sulfate, dextran, dextran sulfate, heparin, heparin sulfate, heparan sulfate, gellan gum, xanthan gum, guar gum, water soluble cellulose derivatives and carrageenan.

In another embodiment of the method, the bead is further coated with a material that extends the release of the labile component from the bead. In a further aspect, the coating is selected from the group comprising of, for example, poly-glycolic acid, PLGA (poly-lactic-co-glycolic acid), collagen, polyhydroxy-alkanoates (PHA), poly-ϵ-caprolactone, poly-ortho esters, poly-anhydrides, poly-phosphazenes, poly-amino acids, polydimethylsiloxane, polyurethranes, poly-tetrafluoroethylene, polyethylene, polysulphone, poly-methyl methacrylate, poly-2-hydroxyethylmethacrylate, polyamides, polypropylene, poly-vinyl chloride, polystyrene and poly-vinyl pyrrolidone.

In one embodiment, the bead is irradiated, and in a further embodiment, the beads are irradiated with gamma-irradiation. In certain embodiments, the bead can be additionally irradiated with UV rays, whereupon, the bead may be free of PPV and MMV viruses.

In several embodiments, the media is a dry-format media, and the labile component to be protected is selected from the group consisting of a polyamine, a growth factor, a cytokine and a vitamin.

In some embodiments, the capsular material is soluble upon reconstitution with an aqueous solvent. In other embodiments, the encapsulating matrix encapsulates a dendrimer-labile component complex. In some embodiments, the dendrimer is a polyamidoamine dendrimer, a polypropylenimine dendrimer, or a polypropylamine (POPAM) dendrimer.

In any of the above embodiments, the methods described can, for example, achieve one or more of the following with respect to the media, feeds, supplements, or functional additives: 1) make them more resistant to irradiation (as measured, for example, based on retetention of efficacy or functionality); 2) increase stability at ambient temperature; 3) allow for extended release of some components; 4) increase stability for transport at ambient temperatures; 5) increase stability to temperature fluctuations.

The compositions used in the methods above may comprise a powdered cell culture medium further comprising a labile compound, and/or at least one concentrated component.

The disclosure is also directed to the following compositions: media, feeds or supplement compositions comprising a microsuspension of a media/feed component. In one embodiment, the medium, feed or supplement composition comprises a mixture of a labile component and an anti-oxidant that is microencapsulated within a capsular matrix into a bead. In a further embodiment, the capsular material is selected from the group comprising, for example, alginate, poly-L-lactic acid, chitosan, agarose, gelatin, hyaluronic acid, chondroitin sulfate, dextran, dextran sulfate, heparin, heparin sulfate, heparan sulfate, gellan gum, xanthan gum, guar gum, water soluble cellulose derivatives and carrageenan. In another embodiment, the bead is coated with a coating solution. In yet another embodiment, the coating solution is selected form the group consisting of poly-glycolic acid, PLGA (poly-lactic-co-glycolic acid), collagen, polyhydroxyalkanoates (PHA), poly-ϵ-caprolactone, poly-ortho esters, poly-anhydrides, poly-phosphazenes, poly-amino acids, polydimethylsiloxane, polyurethranes, poly-tetrafluoroethylene, polyethylene, polysulphone, poly-methyl methacrylate, poly-2-hydroxyethylmethacrylate, polyamides, polypropylene, poly-vinyl chloride, polystyrene, poly-vinyl pyrrolidone, poly-L-lysine and polyornithine.

In a further embodiment, the composition further comprises a chelated reactive species. In a further aspect of this embodiment, the reactive species are either cations, metals ions or trace elements. In another aspect, the chelating moieties are selected from the group comprising EDTA, citrate, succinate, cyclodextrin, clatharates, dendrimers and amino acids.

In any of the compositions described above, the composition can be irradiated. In a further aspect, the irradiation may be with gamma-rays; and in a specific aspect, the gamma-rays may be about 25-100 kGy. In a preferred aspect, gamma-rays of 30-50 kGy are used. In a specific embodiment, the gamma-ray is 30 kGy. One of skill in the art will be capable of determining a level of irradiation that maximizes the objective (for example reduction of live virus or other sterilization) while minimizing the impact on, for example, the functionality of the media or the functionality of a particular component of the media (for example, as measured by a component that is particularly sensitive to irradiation or whatever sterilization technique is being employed).

In one aspect of the invention, the methods described herein may be combined with additional step(s) the goal of which is to measure a functional parameter of the media or composition after sterilization (or after any final processing or finishing step). For example, after irradiation, the sample may be subject to a functional assay for measuring the impact of the irradiation on a particular component or group of components. This step may be used to confirm, for example, that the composition is suitably free of virus and that the components of the media remain in satisfactory condition for the intended application.

In one embodiment, any of the medium, feed or supplement microsuspension and/or encapsulated microsuspension compositions described above are added aseptically, directly into a bioreactor. In another embodiment, any of the any of the medium, feed or supplement microsuspension and/or encapsulated microsuspension compositions described above are place in a porous metal cylinder, that is autoclavable, within a bioreactor.

Any of the media, feeds or supplements described above can be serum-free, protein free, or serum and protein-free. Any of the media, feeds or supplements described above may be specifically designed for suspension cell culture, for mammalian cell culture, for insect cell culture, for hybridoma cell culture, for stem cell culture, for induced pluripotent cell culture, for pluripotent cell culture, for tissue explants and/or organ culture, for three-dimensional culture of cells on artificial cell matrices, and other cell and tissue culture applications that one of skill in the art could adapt the teachings in this disclosure to.

Any of the media, feeds or supplements described above can comprise a powdered cell culture medium, and in a preferred embodiment, the powdered cell culture medium is AGT (advanced granulation technology cell culture medium).

Any of the media, feeds or supplements described above can be used to produce a dry format cell culture medium.

Any of the media, feeds or supplements described above can be increase the shelf life of the cell culture medium.

Any of the media, feeds or supplements described above can be used for recombinant protein production, for vaccine production, for cell production including stem cells, for biofuel production, or for production of nutrients.

Any of the media, feeds or supplements described above can be stored and handled at ambient temperatures, can withstand temperature fluctuations, can withstand HTST and/or UHT pasteurization, can withstand exposure to sterilizing radiation wavelengths such as gamma, UV, and others know in the art.

DETAILED DESCRIPTION

Reference will now be made in detail to various exemplary embodiments. It is to be understood that the following detailed description is provided to give the reader a fuller understanding of certain embodiments, features, and details of aspects of the disclosure, and should not be interpreted as a limitation of the scope of the disclosure.

DEFINITIONS

In order that the present disclosure may be more readily understood, certain terms are first defined. Additional definitions are set forth throughout the detailed description.

The term "advanced granulation technology" or AGT, as used in this application refers to a process of preparing cell culture medium that involves spraying one or more aqueous solutions onto air suspended powdered medium components, with gentle, rapid evaporation of water, under conditions where sensitive components do not lose their efficacy, resulting in an agglomerated granule and a homogenous distribution of the sprayed ingredients throughout the agglomerated granules. The granulated powder (AGT) is discussed in Fike et al., Cytotechnology, 2006, 36:33-39, and in Applicants' patents and/or patent applications: U.S. Pat. No. 6,383,810, issued May 7, 2002; U.S. Pat. No. 7,572,632, issued Aug. 11, 2009; and in U.S. patent application Ser. No. 11/669,827 filed Jan. 31, 2007, whose disclosures are hereby incorporated by reference in their entirety. Briefly, AGT media is a dry, powdered medium that is highly desired in the industry, for properties like large particle size, reduced amount of fine dust while handling, high wetability, low dissolution times into solvent, auto-pH and auto osmolarity maintenance, etc.

Another type of dry powder format is the APM powder which is "advanced powder media", which has advantageous properties of a particle size that is not as fine as DPM powder, but is not as large as AGT granules.

The term "susceptible compound" or "sensitive compound" or "labile compound" as used in this application refers to substance, chemical or compound to be protected from degradation or reaction with "reactive species" present in dry format media. Examples of such compounds in cell culture media include but are not limited to: ethanolamine, vitamins, cytokines, growth factors, hormones, etc.

The term "encapsulating agent" may sometimes be referred to as "sequestering agent" in this application, and refers to the encapsulation, protection, separation, or sequestering of susceptible chemicals or components in the cell culture medium or feed, away from conditions that enhance degradation, or reactivity with other reactive chemicals such as amino acids, trace metal elements such as manganese, copper, etc., inorganic buffers such as sodium bicarbonate and other sodium phosphates; and organic buffers such as MOPS, HEPES, PIPES, etc., which may react slowly with the susceptible compound, thereby making the labile component lose its desirable properties over time. Alternately, encapsulation, protection, separation, or sequestering may be done to protect the susceptible chemical or component from physical damage such as, radiation damage, or heat damage, or physical stress, from exposure to moisture/condensation, or from dehydration, etc. The terms "protect" or "separate" or "sequester" or "encapsulate" may have been used interchangeably in the disclosure, and convey the concept of protecting the susceptible chemical or compound from degrading conditions or chemicals. The "soluble sequestering agent" itself may be soluble upon reconstitution with an aqueous medium, whereupon it releases the "sensitive" encapsulated material. Or, the "insoluble sequestering agent" may be insoluble upon reconstitution with an aqueous medium, whereupon after releasing the "sensitive" encapsulated material, it can be removed by means such as filtration, decanting, etc. from the reconstituted endproduct.

Examples of matrices that may be used for microencapsulation include but are not limited to, alginate, poly-L-lactic acid (PLL), chitosan, agarose, gelatin, hyaluronic acid, chondroitin sulfate, dextran, dextran sulfate, heparin, heparin sulfate, heparan sulfate, gellan gum, xanthan gum, guar gum, water soluble cellulose derivatives, carrageenan and so on.

Optionally, the microcapsules may be coated for one of several reasons: to extend and slowly release the microcapsule components; for protection of labile components against any type of damage, say, radiation, heat, dehydration, etc. Coatings may include but are not limited to, poly-glycolic acid, PLGA (poly-lactic-co-glycolic acid), collagen, polyhydroxy-alkanoates (PHA), poly-$\epsilon$-caprolactone, poly-ortho esters, poly-anhydrides, poly-phosphazenes, poly-amino acids, polydimethylsiloxane, polyurethranes, poly-tetrafluoroethylene, polyethylene, polysulphone, poly-methyl methacrylate, poly-2-hydroxyethylmethacrylate, polyamides, polypropylene, poly-vinyl chloride, polystyrene, poly-vinyl pyrrolidone, etc.

Labile media or feed components include, but are not limited to, compounds such as vitamins, for example, thiamine, B12; amino acids like glutamine; polyamines like ethanolamine; cytokines; growth factors, etc.

Agents used to chelate, deactivate or shut reactive molecules within media include, but are not limited to, compounds such as EDTA, citrate, succinate, cyclodextrin, clatharates, dendrimers, amino acids, etc.

The cell culture medium is preferably a powdered cell culture medium. In one embodiment, the powdered cell culture medium is an advanced granulation technology (AGT) cell culture medium. The cell culture media also refers to feeds, concentrated supplements, concentrated media, and in some instances, liquid media, as applicable.

The terms "cell culture" or "culture" as used in this application refer to the maintenance of cells in an artificial (e.g., an in vitro) environment. It is to be understood, however, that the term "cell culture" is a generic term and may be used to encompass the cultivation not only of individual prokaryotic (e.g., bacterial) or eukaryotic (e.g., animal, plant and fungal) cells, but also of tissues, organs, organ systems or whole organisms, for which the terms "tissue culture," "organ culture," "organ system culture" or "organotypic culture" may occasionally be used interchangeably with the term "cell culture."

The term "cultivation" as used in this application refers to the maintenance of cells in an artificial environment under conditions favoring growth, differentiation, or continued viability, in an active or quiescent state, of the cells. Thus, "cultivation" may be used interchangeably with "cell culture" or any of its synonyms described above.

The terms, "cell culture medium," "culture medium," or "medium" (and in each case plural media) as used in this application refer to a nutritive composition that supports the cultivation and/or growth of cells. The cell culture medium may be a complete formulation, i.e., a cell culture medium that requires no supplementation to culture cells, may be an incomplete formulation, i.e., a cell culture medium that requires supplementation or may be a medium that may supplement an incomplete formulation or in the case of a complete formulation, may improve culture or culture results. The terms "cell culture medium," "culture medium," or "medium" (and in each case plural media) refer to unconditioned cell culture media that has not been incubated with cells, unless indicated otherwise from the context. As such, the terms "cell culture medium," "culture medium," or "medium" (and in each case plural media) are distinguished from "spent" or "conditioned" medium, which may contain many of the original components of the medium, as well as a variety of cellular metabolites and secreted proteins.

The term "powder" or "powdered" as used in this application refers to a composition that is present in granular form, which may or may not be complexed or agglomerated with a solvent such as water or serum. The term "dry powder" may be used interchangeably with the term "powder;" however, "dry powder" as used herein simply refers to the gross appearance of the granulated material and is not intended to mean that the material is completely free of complexed or agglomerated solvent unless otherwise indicated.

A "1× formulation" refers to any aqueous solution that contains some or all ingredients found in a cell culture medium at working concentrations. The "1× formulation" can refer to, for example, the cell culture medium or to any subgroup of ingredients for that medium. The concentration of an ingredient in a 1× solution is about the same as the concentration of that ingredient found in a cell culture formulation used for maintaining or cultivating cells in vitro. A cell culture medium used for the in vitro cultivation of cells is a 1× formulation by definition. When a number of ingredients are present, each ingredient in a 1× formulation has a concentration about equal to the concentration of those ingredients in a cell culture medium. A "1× formulation" of these amino acids contains about the same concentrations of these ingredients in solution. Thus, when referring to a "1× formulation," it is intended that each ingredient in solution has the same or about the same concentration as that found in the cell culture medium being described. The concentrations of ingredients in a 1× formulation of cell culture medium are well known to those of ordinary skill in the art. See Cell Culture Technology for Pharmaceutical and Cell-Based Therapies, 42-50 (Sadettin Ozturk and Wei-Shou Hu eds., Taylor and Francis Group 2006), which is incorporated by reference herein in its entirety. The osmolarity and/or pH, however, may differ in a 1× formulation compared to the culture medium, particularly when fewer ingredients are contained in the 1× formulation.

This disclosure refers to microsuspensions and dried microcapsule beads where the concentration of the same ingredient is concentrated in the micro/nanosuspension, and is concentrated even further in a dry encapsulated bead format. Accordingly, a "7× formulation" is meant to refer to a concentration wherein each ingredient in that micro/nanosuspension or encapsulated bead is about 7 times more concentrated than the same ingredient in the corresponding liquid cell culture medium/feed or supplement. A "10× formulation" is meant to refer to a concentration wherein each ingredient in that micro/nanosuspension or encapsulated bead is about 10 times more concentrated than the same ingredient in the liquid cell culture medium/feed or supplement. As will be readily apparent, "5× formulation," "25× formulation," "50× formulation," "100× formulation," "500× formulation," and "1000× formulation" designate formulations that contain ingredients at about 5 to 25-, 25-50-, 50-70-, 70-100-, 100-500-, 500-1000-fold concentrations, respectively, as compared to a 1× cell liquid medium, feed or supplement. Again, the osmolarity and pH of the media formulation and concentrated solution may vary. A formulation may contain components or ingredients at 1× with respect to a particular cell culture protocol, but at a concentration, for example, 2, 2.5, 5, 6.7, 9, 12 etc.× with respect to a different culture protocol or different base medium.

Microsuspensions

Nutrient feeds, functional additives or supplements are generally provided as clear liquid concentrates or as powders that get reconstituted into clear liquid concentrates for delivery directly into the bioreactor. This means that the components therein are never beyond their solubility limits. If they are prepared beyond their solubility limits, it is well known that precipitate forms, either as flakes or fine precipitates, usually white cloudiness in the bottle. Settling of these components occur in several hours, which means that the concentrated solution cannot be used to deliver accurate amounts of feed.

This disclosure provides techniques for preparing a medium, feed and/or supplement components in such a way that the concentrated components do not precipitate out. This is achieved by making a microsuspension and/or nanosuspension (also referred to as micro/nanosuspension) from a dry powder cell culture medium or feed that has one or more concentrated component.

A micro/nanosuspension is a micron/nano-sized solid in an aqueous solvent base that, in one embodiment, does not separate over time. Micro/nanosuspensions, for example, provide a means of concentrating one or more media/feed components beyond the solubility limit of that component. Some desirable properties of micro/nanosuspensions include, but are not limited to, enabling increased nutrient supplement concentrations (e.g., amino acids) in minimal volume; extremely rapid dissolution of micro/nanosuspensions components in aqueous solutions (more rapid than the media would dissolve absent such preparation); capacity for encapsulation (i.e. for sterilization and protection of components in encapsulated form); capacity for direct addition of sterile, micro/nanosuspensions beads into pre-existing cultures in a bioreactor; the ability to increase efficiency and manufacturing processes in a bioreactor.

Microsuspensions have been prepared in other industries, for example, in the pharmaceutical or cosmetic industry, generally using two approaches: i) a top-down approach, and ii) a bottom-up approach. In the top-down approach, the particles of a dry powder are broken down by a milling process such as a Fitz® mill (the industry standard for precise particle size reduction), until microsuspensions are obtained, or by wet-milling or by using a microfluidizer to obtain nanosuspensions. In the bottom-up approach, components within a solution are gradually precipitated out by gentle manipulation of parameters like pH, or polymerization parameters, until micro/ or nanosuspensions are obtained. These methods were not useful in preparing the micro/ or nanosuspensions described here. Given the sensitive nature of the media and supplements utilized herein, applicants recognized the need for a novel method for preparing these micro/ or suspensions of media, feeds. As described in Example 1 and in FIG. 1, applicants started with a dry media, feed or supplement powder, and by adding a minimal amount of WFI water to the dry powder, vigorously mixing the slurry into a homogenous paste such that all particles were coated with an aqueous phase, micro/nanosuspensions were formed. As one of skill in the art would know in light of the disclosure herein, any aqueous base beside water, for example, buffer, balanced salt solution, a liquid medium, or any solution comprising one or more media components including amino acids, lipids, etc., may be added to any powdered formulation to make a micro/nanosuspension described in this disclosure. One of skill may further adapt any of the steps or materials used in the suggested protocol: for instance, the sequence of addition steps, the sequence and number of mixing steps, the volume of liquid, the mixing time, the apparatus or device for mixing the slurry to homogeneity, the media or feed formulation, etc. and they would know how to manipulate the conditions to suit the consistency and nature of the desired micro/nanosuspension.

In one embodiment, any structural or informational molecule, any nutrient, required by a cell in culture can be made into a micro/nanosuspension using the techniques, or variations of the techniques described here. Besides media and feeds, examples of structural and/or informational molecules may include, but are not limited to, vitamins, amino acids, peptides, macromolecules, anti-oxidants, hormones, growth factors, and so on. In certain embodiments, micro/nanosuspensions of cellular scaffolding matrices complexed with cellular nutrients may be made in order to grow cells within the suspensions three dimensionally.

The micro/nanosuspension compositions prepared as described above may be useful in many applications, for example, in nutrient supplementation to significantly boost component concentrations beyond the level of solubility of the component in question, such that, volume of addition to the reactor is minimal; or, for encapsulating the microsuspensions, as described below, and making a dried form of the encapsulated bead resulting in a "super concentrated" supplement that can be directly added to the bioreactor, which has not been done before.

In one embodiment, microsuspensions can be made from any form of dry powder, of any component that needs to be provided in culture in a concentrated form, and provide at least a 2 to 5-fold, 5 to 10-fold, 10 to 15-fold, 15 to 20-fold, 20 to 25-fold, 25 to 30-fold, 30 to 50-fold, 50 to 70-fold, 70 to 100-fold concentration of the component in the microsuspension over an equivalent liquid concentrate or feed having the same component in solution.

Microencapsulation

Figure 3:
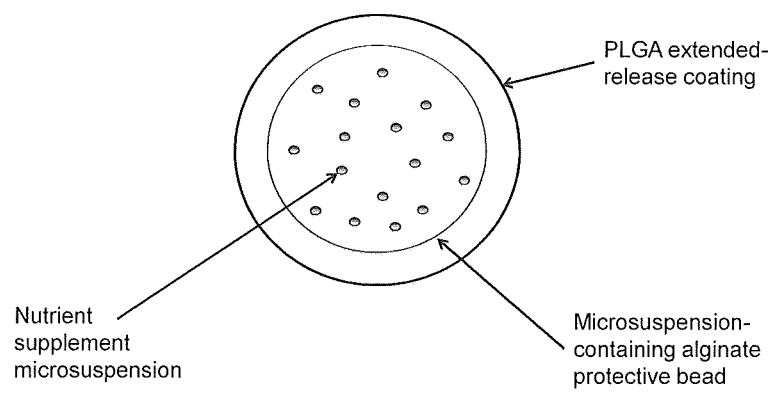
FIG. 3 a schematic representation of an encapsulated microsuspension bead, which is additionally coated for extended release.
Figure 4:
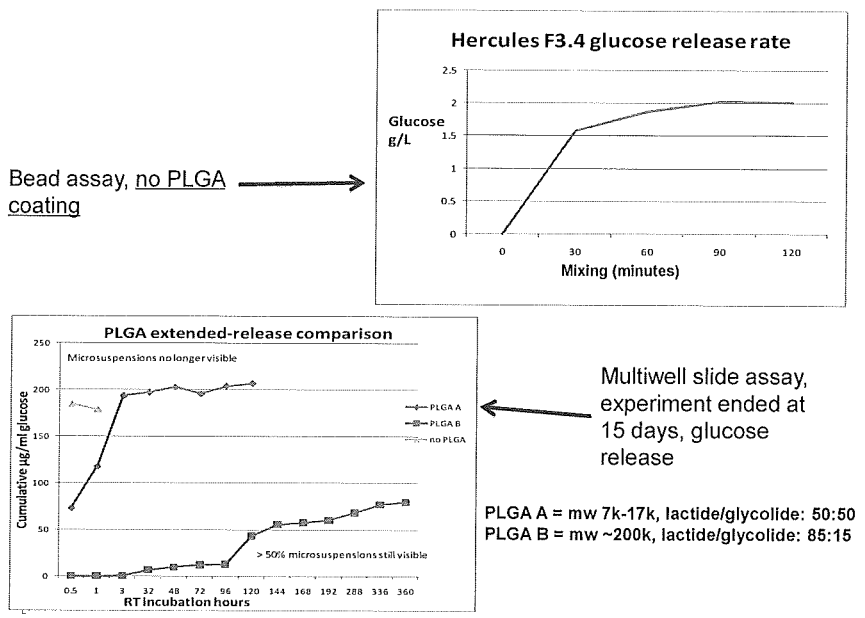
FIG. 4 shows the impact of PLGA coating on delaying the release of components from within the microencapsulated microsuspension preparations. a) top panel: no coating; b) bottom panel: comparison of coating with PLGA A and PLGA B. A and B have different ratios of lactide:glycolide. PLGA B with an 85:15 ratio showed good extended release properties and maintained its shape an ability to release components >15 days in solution.
Figure 5:
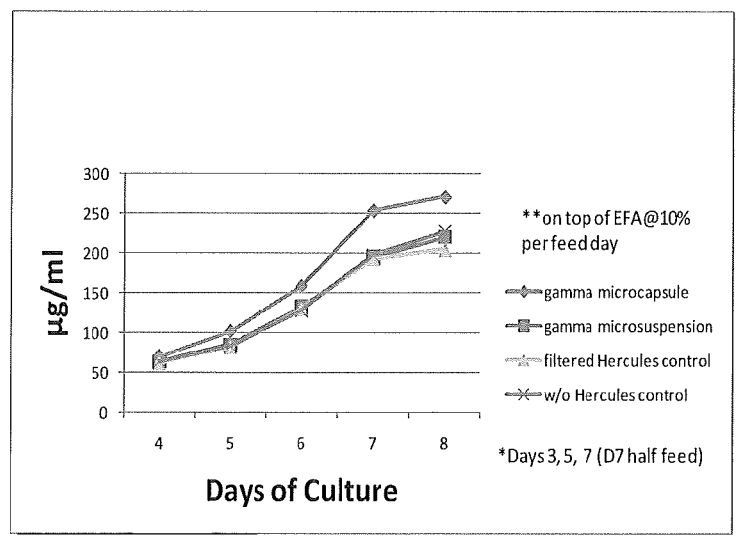
FIG. 5 shows the effect of irradiation on the preparations of this disclosure. Comparison of protein production efficiency in cells cultured with i) irradiated microsuspensions, ii) dry, encapsulated microsuspensions are similar to those in iii) control, non-irradiated, liquid feed, which was sterilized by filtration.
Figure 6:
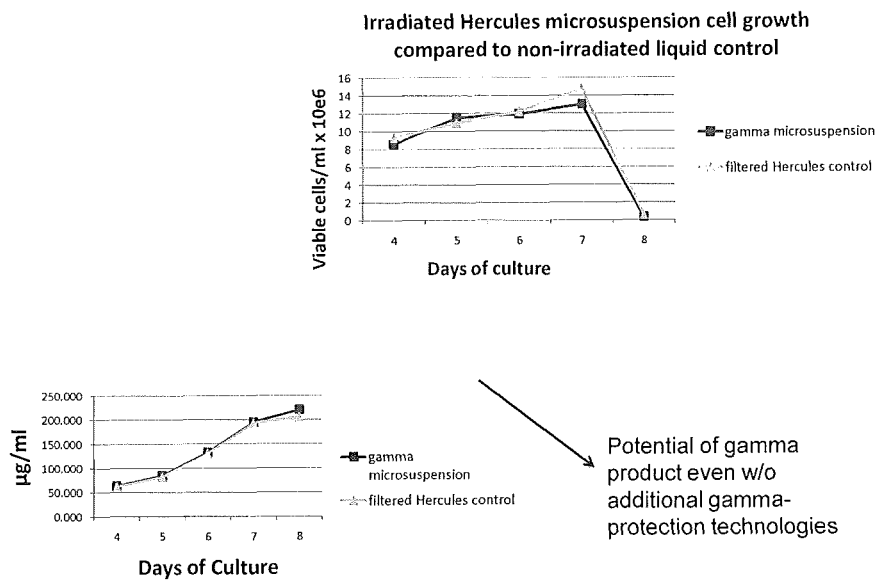
FIG. 6 shows that irradiation, at approx. 30 kGy, does not negatively impact (a) cell growth (top panel); or, (b) protein production (bottom panel), while culturing cells in an irradiated test feed. Additional supplements 68 and 86 were also tested and showed similar results (data not shown).

This disclosure provides a method of microencapsulating the micro/nanosuspension described above, that was made from a dry powdered cell culture medium, feed, supplement or concentrate. The resulting encapsulated products may be referred to as 'microcapsules', 'encapsulated bead', 'beads', 'capsules' or 'microbeads' in this disclosure. When the encapsulated micro/nanosuspension is dried into beads, the drying step provides a greater degree of concentration of the encapsulated micro/nanosuspensions. Microencapsulation may be done, for example, to "keep apart" or sequester sensitive or labile components in a complex mixture such as cell culture media/feed. Thus, encapsulation may yield higher concentrations of certain feed components such as, for example, amino acids, so that these feeds can be directly added as concentrated, high nutrient supplements into any culture system, for example, in fed-batch cultures. Further coating of the capsule may affect delayed-release of nutrients to into cell cultures (discussed below). Encapsulation can be done by: (a) a standard microencapsulation process of microsuspensions and nanosuspensions for "gently-releasing" some or all components over several hours; (b) an alternative bead-gelling process to significantly retard the internal component release. An exemplary demonstration of delayed release can be found in the Examples and in FIGS. 3, 4 and 8.

In one specific embodiment, the agent used to encapsulate or embed the labile component was alginate. Alginate microcapsules have been used for many purposes, including drug delivery and the immobilization of cells growing in cell culture to enhance cell growth and viability. See e.g., Serp et al., Biotechnology and Bioengineering, 2000, 70(1):41-53; Breguet et. al., Cytotechnology, 2007, 53:81-93; Chayosumrit et al., Biomaterials, 2010, 31:505-14; U.S. Pat. No. 7,482,152; and U.S. Pat. No. 7,740,861, all of which are incorporated by reference in their entirety.

The encapsulation technique was also described in Applicants' co-pending application, PCT/US2012/024194, which described entrapping certain labile, sensitive or susceptible compounds such as ethanolamine, vitamins, growth factors like insulin, etc. in capsular materials, including but not limited to, alginate.

Without intending to be bound by any theory, it appears that encapsulating or embedding sensitive components within another molecule reduces the labile compound's direct contact with other components or conditions that promote its degradation, or reduces its stability. Methods describing the preparation of microcapsules for the reduction of ethanolamine degradation by microencapsulation is described in Applicant's co-pending application, PCT/US2012/024194, filed Feb. 7, 2012, whose disclosure is incorporated by reference herein in its entirety. Although those methods were primarily exemplified within the context of ethanolamine stabilization, they can be used/adapted to stabilize any susceptible or labile chemical or compound in a media, feed or supplement. It is understood that the microencapsulation methods described therein can be used for stabilizing any susceptible compound required for cell culture, including but not limited to, vitamins like thiamine, B12, etc., unstable amino acids such as glutamine, cytokines, growth factors, sensitive and valuable proteins or peptides, etc. and for enhanced delivery of the stabilized compound, and can be applied to fields beyond cell culture media development. In this disclosure, the encapsulation technique was adapted to micro/nanosuspension beads, which required adaptation of several steps and techniques. For instance, the entrapping steps for susceptible compounds in the PCT/US2012/024194 application lacked several steps. For encapsulation of microsuspensions, the capsular material, such as alginate, was mixed and blended with the microsuspension. This mix was then aspirated into a dispensing device such as a pipette or a dropper and droplets of encapsulated microsuspension were gradually generated by dropping the mix gently onto a non-stick surface, for example, on parafilm. Then, a cross-linking agent was added to the drop to form beads. These beads were desiccated and vacuum dried to remove moisture, and are generally referred to as "encapsulated microsuspension beads" or just "beads".

As one of skill in the art would know based on the instant disclosure, one may adapt any of the steps or the materials used in the suggested protocol (see Example 2). For instance, a variety of capsular materials may be used, or a variety of drop delivery devices including pipettes, droppers, syringes or any adaptation thereof may be used, or any cross-linking agent may be used, or the bead may be dried or desiccated by a variety of means and to differing degrees of dryness and/or hardness. One of skill in the art will be able to determine appropriate encapsulating agents for the purpose at hand, for instance, alginate, poly-L-lactic acid (PLL), chitosan, agarose, gelatin, hyaluronic acid, chondroitin sulfate, dextran, dextran sulfate, heparin, heparin sulfate, heparan sulfate, gellan gum, xanthan gum, guar gum, water soluble cellulose derivatives, carrageenan and so on.

Microcapsules are typically spherical particles having a diameter of 2 mm or less, usually within the diameter range of 0.05-1.5 mm. Typically, alginate microcapsules are formed by crosslinking between the polyanionic alginate and a divalent or trivalent polyvalent cation, such as calcium chloride. Other salts for cross-linking may be divalent or trivalent cations, such as magnesium chloride, barium chloride, and aluminum sulfate.

Encapsulation has several advantages, some of which include, but are not limited to, protection of labile components from degradation, or from unwanted reactions; or to delay and/or extend the release-time of the encapsulated components into cell culture In one embodiment, protection due to microencapsulation of media; or to increase the stability and storage of cell culture media, feeds and supplements comprising labile compounds at ambient temperatures. The encapsulated compound can be dried into beads, which can then be blended and/or mixed with other media components. Accordingly, micro/nanosuspensions may result in a 1-5%, 5-10%, 10-15%, 15-20%, 20-25%, 25-30%, 30-35%, 35-40%, 40-50%, 50-60%, 60-70%, 70-80%, 80-90%, or 90-100% reduction in any loss of media/labile component functionality, which may be measured by a suitable functional assay for the encapsulated labile or media component, using techniques known in the art, including the methods disclosed in this application. Examples of functional assays may be, the ability of a media/feed composition comprising microcapsules to increase the cell viability over days, or the cell number in a culture system, or recombinant protein production, or an increase in the amount and/or the function of a recombinant protein being expressed (for example, an enzyme or a receptor functional assay, or the stability of an encapsulated labile component like glutamine can be evaluated during culture, etc., as would be known to one of skill in the art).

In one embodiment, a sequestering agent like alginate was used to encapsulate or embed an ethanolamine-dendrimer complex. Dendrimers are hyper-branched synthetic macromolecules that can be made using controlled sequential processes to give them defined structural and molecular weight characteristics; reviewed in Astruc et al., Chem. Rev. 2010, 110:1857-1959, which is hereby incorporated by reference in its entirety. Dendrimers can be used to prepare the encapsulated microsuspensions of the instant invention as well. In another embodiment, the dendrimer used in the methods as described in PCT/US2012/024194 was poylamidoamine, and it may be adapted for used in encapsulated micro/nanosuspensions. Other dendrimers that can be used in the methods described in this application include, but are not limited to polypropylenimine (PPI) dendrimers, phosphorous dendrimers, polylysine dendrimers, polypropylamine (POPAM) dendrimers, polyethylenimine dendrimers, iptycene dendrimers, aliphatic poly(ether) dendrimers, or aromatic polyether dendrimers.

In one embodiment, microencapsulated micro/nanosuspensions can be made for any component that needs to be provided in culture in a concentrated form, and provides at least a 2 to 5-fold, 5 to 10-fold, 10 to 15-fold, 15 to 20-fold, 20 to 25-fold, 25 to 30-fold, 30 to 50-fold, 50 to 70-fold, 70 to 100-fold concentration of the component in the encapsulated micro/nanosuspension over an equivalent liquid concentrate or feed having the same component in solution. In one exemplary embodiment, the microsuspension preparation of a concentrated feed preparation as seen in the Figures was about 7-fold more concentrated than its corresponding liquid feed, whereas the dried encapsulated form of the same microsuspension was about 10-fold more concentrated than its corresponding liquid feed.

Anti-Oxidants

This disclosure also describes that the labile compounds within the capsule may be further combined with one or more protective substances, such as anti-oxidants, prior to the encapsulation process. Therefore, in certain embodiments, a mixture anti-oxidant and a labile component in a powdered media, feed, or supplement may be used as a starting material to prepare the microsuspension preparation, prior to encapsulation. Exemplary anti-oxidants include, but are not limited to, vitamins like ascorbic acid, beta-carotene, vitamin A, E, lycopene, flavanoids, selenium, etc. Effects of anti-oxidants on protection due to irradiation is depicted in FIG. 8.

In one embodiment, protection due to the anti-oxidants prior to microencapsulation may result in a 1-5%, 5-10%, 10-15%, 15-20%, 20-25%, 25-30%, 30-35%, 35-40%, 40-50%, 50-60%, 60-70%, 70-80%, 80-90%, or 90-100% reduction in loss of media/labile component functionality, which may be measured by a suitable functional assay for the labile or media component. The dried microcapsule beads can then be blended into and/or mixed with other media components.

Chelation

This disclosure also describes chelation agents, which are agents that chelate, deactivate or shut off reactive molecules found within media that include cations, metals ions, trace elements, etc. Reactive molecules interact adversely with labile compounds in media and reduce their efficacy. By chelating/complexing the reactive compounds, compounds such as EDTA, citrate, succinate, cyclodextrin, clatharates, dendrimers, amino acids, etc. reduce their reactivity. In addition, chelates may be designed to remain partitioned outside a microcapsule/bead comprising a labile compound. The effect of chelation on the protection of labile compounds is described in FIG. 9.

In one embodiment, protection due to chelation of reactive and/or ROS producing media/feed components outside the microcapsule may result in a 1-5%, 5-10%, 10-15%, 15-20%, 20-25%, 25-30%, 30-35%, 35-40%, 40-50%, 50-60%, 60-70%, 70-80%, 80-90%, or 90-100% reduction in loss of media/labile component functionality, which may be measured by a suitable functional assay for a labile or media component. Examples of functional assays may be, the ability of a media/feed composition comprising microcapsules and chelated components to increase the cell viability over days, or the cell number in a culture system, or recombinant protein production, or an increase in the amount and/or the function of a recombinant protein being expressed (for example, an enzyme or a receptor functional assay, or the stability of an encapsulated labile component like glutamine can be evaluated during culture, etc., as would be known to one of skill in the art).

Delayed-Release

In one embodiment, optionally, the microcapsule can further be coated with protective coatings like PLGA for delayed-release or extended-release of components within the microcapsule. Typical medium components for delayed release may include, but are not limited to, vitamins, glucose, amino acids, growth factors or cytokines. Components can be released from within the same microcapsule at the same rate, or released from different microcapsules at different rates and at different times, depending on the delayed-release formulation. An exemplary use for such a dual-format, delayed release medium would be in the release of growth components (for e.g., glucose, amino acids, etc.) early in the culture followed by release of productivity components (for e.g., recombinant protein expression inducers such as galactose, etc.) later into the post-log phase of the culture. Such a medium would need no customer action as the dual-format medium would take care of the timely release of necessary components. Another example would be in maintaining two or more components separate until a designated time when they need to react together within a culture for a specific purpose.

Coating solutions that may be used to coat after microencapsulation, may be applied to provide additional layers, and include, but are not limited to, poly-glycolic acid, PLGA (poly-lactic-co-glycolic acid), collagen, polyhydroxyalkanoates (PHA), poly-ε-caprolactone, poly-ortho esters, poly-anhydrides, poly-phosphazenes, poly-amino acids, polydimethylsiloxane, polyurethranes, poly-tetrafluoroethylene, polyethylene, polysulphone, poly-methyl methacrylate, poly-2-hydroxyethylmethacrylate, polyamides, polypropylene, poly-vinyl chloride, polystyrene, poly-vinyl pyrrolidone, poly-L-lysine or polyornithine. Encapsulated components that are formed into beads and externally coated may themselves be further encapsulated so that a wide range of release options are available depending upon the coating characteristics of the surrounding coating and the individual bead coatings.

The additional outer coating may be selected from alginate, poly-L-lactic acid, chitosan, agarose, gelatin, hyaluronic acid, chondroitin sulfate, dextran, dextran sulfate, heparin, heparin sulfate, heparan sulfate, gellan gum, xanthan gum, guar gum, water soluble cellulose derivatives and carrageenan. Effects of coating are demonstrated and discussed in the Examples and in FIGS. 3, 4 and 8. In one embodiment, delayed-release of internal components from a microcapsule may result in maintenance of the encapsulated component in a cell culture system over 6-24 hours, 24-48 hours, 48-72 hours, over 1 day, 2 days, 3-5 days, 5-10 days, 10-15 days, 15-20 days, 20-25 days, 25-30 days, 30-40 days, 40-50 days, over the duration of the culture. Delayed release may be measured by a suitable time-release assay for a labile or media component within the capsule, and may optionally be coated for extended release as well. An exemplary time release assay is discussed below. Other examples of functional assays may be, the ability of a media/feed composition comprising coated microcapsules to increase the cell viability over days, or the cell number in a culture system, or recombinant protein production, or an increase in the amount and/or the function of a recombinant protein being expressed (for example, an enzyme or a receptor functional assay, or the stability of an encapsulated labile component like glutamine can be evaluated during culture, etc., as would be known to one of skill in the art).

Besides the typical medium components like vitamins, glucose, amino acids, growth factors or cytokines, the following cell culture nutrients/reagents may also be targeted for delayed-release. They include, but are not limited to, all chemicals or compositions that are used to promote cell metabolism whether for growth or product synthesis and secretion such as glucose and other forms of hexose, amino acids, salts, peptides, proteins such as collagen and protein fractions, lipids, hormones, vitamins, nucleotides/nucleosides, trace elements, ribonucleotides/ribonucleosides, sera, sera fractions such as bovine albumin and ceruloplasmin, and other components that are not directly metabolized but provide cell culture-related advantages to cells in culture, such as pluronic of various types such as F68 which prevent cell clumping, fibronectin and peptide sequences such as RGD to support cell attachment and anti-foam reagents. In addition to single or multiple individual components, mixtures of components may be included in this delay-release methodology. The powder itself may be either in fine-milled or granulated (AGT) format.

An Exemplary Assay to Detect Delayed-Release

Detection of release-delay involves assaying over a period of time for the component(s) in question and observing an increase over time. An example for a typical CHO cell nutrient supplement would be measuring for glucose. The supplement containing glucose would be added to water and a T=0 sample withdrawn and held. Then at subsequent time periods (such at 24, 48, 72 hours) additional samples can be withdrawn. If there were a delayed-release component in the supplement, then glucose would be seen rising over time. One assay for measuring glucose would be measurement of glucose oxidase, which is commercially available in kit format. The principle here is that glucose oxidase reacts with glucose to yield gluconic acid and hydrogen peroxide. The hydrogen peroxide reacts with o-dianisidine to yield oxidized o-dianisidine, which forms a pink color upon exposure to sulfuric acid. This can be read spectrophotometrically. Another assay for glucose measurement or for other supplement components such as amino acids would be by HPLC. The method would measure a continual increase of the release component over time, which is the hallmark of delayed-release.

Sterilization

In this disclosure, a labile, sensitive or susceptible compound includes but is not limited to substances sensitive to physical, chemical, radiation degradation/destruction. Typical sensitive media substances may be sensitive to chemical interaction with a reactive oxygen species, sensitive to metals including trace metals, sensitive to high temperature, to irradiation (gamma, X-ray, UV, ionizing, etc.), to freezing temperatures, to freeze-thaw, to pressure, agitation, etc. In a further aspect of this embodiment, trace elements or substances generating reactive oxygen species (ROS), etc. may be chelated and/or kept on the exterior of the microcapsule comprising the labile component.

This disclosure provides a means for sterilizing a media comprising encapsulated components using irradiation while protecting the irradiation labile components, for example, through anti-oxidant coating and/or subsequent encapsulation. Sterilizing irradiation includes wavelengths of light such as gamma rays, UV rays, and other ionizing radiation. Sterilizing gamma irradiation used may be from 5 kGy to 100 kGy. In one embodiment, the medium comprising encapsulated components can be sterilized by gamma irradiation of up to about 50 kGy without loss of media or feed functionality, and/or with about 8-log reduction of virus. This satisfies a SAL (Sterility Assurance Level) of $>10e^{-8}$ of the porcine parvo virus (PPV) and/or the murine minute virus (MMV). In some embodiments, the medium comprising encapsulated components can be sterilized by a combination of gamma irradiation greater than 50 kGy up to 100 kGy without loss of media or feed functionality.

In certain embodiments, about 6-8 logs of SAL, or reduction of viruses like MMV and PPV were observed. In combination with other sterilization technologies such as UV irradiation, further reduction of SAL was possible, up to about 8 logs of SAL without loss of media or feed functionality. In addition, the reconstituted media can be pasteurized by techniques such as HTST (high temperature short time) or UHT (ultra high temperature), and/or by filtration through anti-viral filters of pore size 0.1-0.2 μm, which may provide further reduction of viruses such as vesivirus, porcine circovirus, and other small enveloped viruses that are problematic in the biotechnology industry, without loss of media or feed functionality.

Due to their ability to be sterilized, and because there is no loss of media or feed functionality, the compositions of this disclosure would fit into an enhanced cell culture workflow and improve bioreactor productivity as they can added into a bioreactor directly during the pre-existing culture of a cell. In certain embodiments, the addition can be either as encapsulated beads, or in other embodiments, additions may be as micro/nanosuspensions. Another example would be in the direct addition of the sterile microcapsules into the bioreactor, addition of filtered water, mixing and then addition of cells.

Microcapsules could be used for nutrient supplementation in bioreactors in at least two ways: 1) Sterile microcapsules could be added directly to the bioreactor where they release components in a time-release manner (right), or 2) they may be added to a porous metal cylinder, cage, or any similar apparatus, with about 0.22µ pore size, keeping the beads away from contacting the cells in culture. With option 1, the beads may interfere with filtration, or may reduce cell count or productivity. With option 2, bioreactor stirring alone is enough to dissolve nutrient supplement from inside the porous metal cage and to pass into the bioreactor.

Cell Culture Media

A cell culture medium is composed of a number of ingredients and these ingredients vary from one culture medium to another. A cell culture medium may be a complete formulation, i.e., a cell culture medium that requires no supplementation to culture cells, may be an incomplete formulation, i.e., a cell culture medium that requires supplementation or may be a supplement that is used to supplement an incomplete formulation or in the case of a complete formulation, may improve culture or culture results.

Generally, upon reconstitution, a cell culture medium will have solutes dissolved in solvent. The solutes provide an osmotic force to balance the osmotic pressure across the cell membrane (or wall). Additionally the solutes will provide nutrients for the cell. Some nutrients will be chemical fuel for cellular operations; some nutrients may be raw materials for the cell to use in anabolism; some nutrients may be machinery, such as enzymes or carriers that facilitate cellular metabolism; some nutrients may be binding agents that bind and buffer ingredients for cell use or that bind or sequester deleterious cell products.

Depending on the cell and the intended use of the cell, the ingredients of the cell culture medium will optimally be present at concentrations balanced to optimize cell culture performance. Performance will be measured in accordance with a one or more desired characteristics, for example, cell number, cell mass, cell density, O2 consumption, consumption of a culture ingredient, such as glucose or a nucleotide, production of a biomolecule, secretion of a biomolecule, formation of a waste product or by product, e.g., a metabolite, activity on an indicator or signal molecule, etc. Each or a selection of the ingredients will thus preferably optimized to a working concentration for the intended purpose.

A basal medium is typically used for maintenance of a cell culture, and can comprise a number of ingredients, including amino acids, vitamins, organic and inorganic salts, sugars and other components, each ingredient being present in an amount which supports the cultivation of the cell in vitro.

The media described herein that comprises microsuspensions and/or encapsulated microsuspensions can be a 1× formulation or can be concentrated, for example, as a 5×, 10×, 20×, 50×, 500×, or 1000× medium formulation. If the individual medium ingredients are prepared as separate concentrated solutions, an appropriate (sufficient) amount of each concentrate is combined with a diluent to produce a 1× medium formulation. Typically, the diluent used is water but other solutions including aqueous buffers, aqueous saline solution, or other aqueous solutions may be used. The media could be a basal media to which additional components need to be added, or a complete media which requires no additional additives and is capable of growing cells once reconstituted.

In one embodiment, the reconstituted media from the dry powder that comprises microsuspensions and/or encapsulated microsuspensions results in an auto-pH and/or auto-osmolality medium/feed in that, it has balanced buffer concentrations and/or salt concentrations that contribute to automatically achieving a desired pH and osmolality suitable for growing a certain cell type without additional pH or salt concentration adjustment.

In another embodiment, or in a further embodiment, the reconstituted media from the dry powder that comprises microsuspensions and/or encapsulated microsuspensions results in a chemically defined cell culture medium. The presence of media proteins makes purification of recombinant protein difficult, time-consuming, and expensive and can also lead to reduced product yields and/or purity. Thus, in one embodiment, the cell culture medium would be serum-free and protein-free, yet complete, such that it can support the growth of a particular cell type. Alternately, the reconstituted media from the dry powder could be serum-free but still contain proteins derived from one or more non-animal derived sources (animal origin free—AOF) like from plants, yeast, algal, fungal, or recombinant sources such as bacteria, fungal, plant, yeast algal, etc. in the form of hydrolysates, or in the form of a purified protein or an hydrolysate fraction. In other instances, serum-free media may still contain one or more of a variety of animal-derived components, including albumin, fetuin, various hormones and other proteins. In another embodiment, the medium or media supplement is protein free and further, does not contain lipids, hydrolysates, or growth factors.

The media or supplements of this disclosure compr used for fed-batch cultivation. Fed-batch cultivation of cells is typically used for industrial production of biomolecules, such as proteins to increase cell concentration and to extend culture lifetime for a high product concentration and volumetric productivity. Fed-batch cultures involve the controlled addition of one or more nutrients, such as glucose, to a basal medium. The nutrient(s) help to control the growth of the cell culture by preventing nutrient depletion or accumulation and byproduct accumulation, thereby maintaining important parameters, such as osmolality and CO2 concentration, within levels that promote cell growth or minimize cell death for optimal product expression.

Cells and Viruses

Media/feeds containing microsuspensions and/or encapsulated microsuspensions, as described herein, can also be used to culture a variety of cells. In one embodiment, the media is used to culture eukaryotic cells, including plant or animal cells, such as mammalian cells, fish cells, insect cells, algal cells, amphibian cells or avian cells or to produce viruses, virus-like particles.

Mammalian cells that can be cultured with the media/feeds described herein include primary epithelial cells (e.g., keratinocytes, cervical epithelial cells, bronchial epithelial cells, tracheal epithelial cells, kidney epithelial cells and retinal epithelial cells) and established cell lines and their strains (e.g., 293 embryonic kidney cells, BHK cells, HeLa cervical epithelial cells and PER-C6 retinal cells, MDBK (NBL-1)

cells, 911 cells, CRFK cells, MDCK cells, CHO cells, BeWo cells, Chang cells, Detroit 562 cells, HeLa 229 cells, HeLa S3 cells, Hep-2 cells, KB cells, LS180 cells, LS174T cells, NCI-H-548 cells, RPMI 2650 cells, SW-13 cells, T24 cells, WI-28 VA13, 2RA cells, WISH cells, BS-C-I cells, LLC-MK2 cells, Clone M-3 cells, 1-10 cells, RAG cells, TCMK-1 cells, Y-1 cells, LLC-PK1 cells, PK(15) cells, GH1 cells, GH3 cells, L2 cells, LLC-RC 256 cells, MH1C1 cells, XC cells, MDOK cells, VSW cells, and TH-I, B1 cells, or derivatives thereof), fibroblast cells from any tissue or organ (including but not limited to heart, liver, kidney, colon, intestines, esophagus, stomach, neural tissue (brain, spinal cord), lung, vascular tissue (artery, vein, capillary), lymphoid tissue (lymph gland, adenoid, tonsil, bone marrow, and blood), spleen, and fibroblast and fibroblast-like cell lines (e.g., CHO cells, TRG-2 cells, IMR-33 cells, Don cells, GHK-21 cells, citrullinemia cells, Dempsey cells, Detroit 551 cells, Detroit 510 cells, Detroit 525 cells, Detroit 529 cells, Detroit 532 cells, Detroit 539 cells, Detroit 548 cells, Detroit 573 cells, HEL 299 cells, IMR-90 cells, MRC-5 cells, WI-38 cells, WI-26 cells, MiC11 cells, CHO cells, CV-1 cells, COS-1 cells, COS-3 cells, COS-7 cells, Vero cells, DBS-FrhL-2 cells, BALB/3T3 cells, F9 cells, SV-T2 cells, M-MSV-BALB/3T3 cells, K-BALB cells, BLO-11 cells, NOR-10 cells, C3H/lOTl/2 cells, HSDM1C3 cells, KLN2O5 cells, McCoy cells, Mouse L cells, Strain 2071 (Mouse L) cells, L-M strain (Mouse L) cells, L-MTK-(Mouse L) cells, NCTC clones 2472 and 2555, SCC-PSA1 cells, Swiss/3T3 cells, Indian muntjac cells, SIRC cells, CII cells, and Jensen cells, or derivatives thereof).

Eukaryotic cells, including algal cells, may also be cultivated in the media compositions of this disclosure comprising microsuspensions and/or encapsulated microsuspensions, to produce biofuels, under suitable conditions for growth and biofuel production.

Cells supported by the culture medium described herein can also be derived from any animal, preferably a mammal, and most preferably a mouse or a human. Cells cultured according to the methods disclosed herein may be normal cells, diseased cells, transformed cells, mutant cells, somatic cells, germ cells, stem cells, precursor cells or embryonic cells, any of which may be established or transformed cell lines or obtained from natural sources. Cells may be used for experimental purposes or for production of useful components.

In one embodiment, the media described herein is used to culture Chinese Hamster Ovary (CHO) cells, including recombinant CHO cells or CHO-derived cell lines like CHOS, CHOK1, DG44, RevO, etc. The term CHO cell includes reference to recombinant CHO cells and to all CHO-derived cell lines described. CHO cells have been classified as both epithelial and fibroblast cells derived from the Chinese hamster ovary. A cell line started from Chinese hamster ovary (CHO-K1) (Kao, F.-T. And Puck, T. T., Proc. Natl. Acad. Sci. USA 60: 1275-1281 (1968) has been in culture for many years but its identity is still not confirmed. Most biopharmaceuticals currently produce proteins in CHO cells for many advantages that the cell line has, such as human-like glycosylation patterns, precise post-translation modification and low risk for transmission of human viruses.

Cultivation of Cells

Cells supported by the culture medium described herein can be cultivated according to the experimental conditions determined by the investigator. It is to be understood that the optimal plating and culture conditions for a given animal cell type can be determined by one of ordinary skill in the art using only routine experimentation. For routine monolayer culture conditions, using the cell culture media described herein, cells can be plated onto the surface of culture vessels without attachment factors. Alternatively, the vessels can be pre-coated with natural, recombinant or synthetic attachment factors or peptide fragments (e.g., collagen, fibronectin, vitronectin, laminin and the like, or natural or synthetic fragments thereof), which are available commercially for example from Life Technologies, Corp. (Carlsbad, Calif. R&D Systems, Inc. (Rochester, Minn.), Genzyme (Cambridge, Mass.) and Sigma (St. Louis, Mo.). Cells can also be seeded into or onto a natural or synthetic three-dimensional support matrix such as a preformed collagen gel or a synthetic biopolymeric material. For suspension cultivation, cells are typically suspended in the culture media described herein and introduced into a culture vessel that facilitates cultivation of the cells in suspension, such as a spinner flask, perfusion apparatus, or bioreactor. Ideally, agitation of the media and the suspended cells will be minimized to avoid denaturation of media components and shearing of the cells during cultivation.

The cell seeding densities for each experimental condition can be optimized for the specific culture conditions being used. For routine monolayer culture in plastic culture vessels, an initial seeding density of $1-5\times10^5$ cells/cm2 is preferable, while for suspension cultivation a higher seeding density (e.g., 5-20×105 cells/cm2) may be used.

Mammalian cells are typically cultivated in a cell incubator at about 37° C. The incubator atmosphere should be humidified and should contain about 3-10% carbon dioxide in air, more preferably about 8-10% carbon dioxide in air and most preferably about 8% carbon dioxide in air, although cultivation of certain cell lines may require as much as 20% carbon dioxide in air for optimal results. Culture medium pH should generally be in the range of about 6.2-7.8, preferably about 7.1-7.4, and most preferably about 7.1-7.3. The cells may be cultured under different conditions (pH, temperature and/or carbon dioxide) to enhance protein production.

Cells in closed or batch culture should undergo complete medium exchange (i.e., replacing spent media with fresh media) when the cells reach a density of about 1.5-2.0×106 cells/ml. Cells in perfusion culture (e.g., in bioreactors or fermenters) will receive fresh media on a continuously recirculating basis.

Virus and Vaccine Production

In addition to cultivation of cells in suspension or in monolayer cultures, the present media may be used in methods for producing viruses from mammalian cells. Such methods comprise (a) contacting a cell (e.g., a mammalian cell) with a virus under conditions suitable to promote the infection of the cell by the virus; and (b) cultivating the cell in the culture media described herein under conditions suitable to promote the production of virus by the cell. The cell may be contacted with the virus either prior to, during or following cultivation of the cell in the culture media. Optimal methods for infecting a mammalian cell with a virus are well-known in the art and will be familiar to one of ordinary skill. Virus-infected mammalian cells cultivated in the culture media described herein may be expected to produce higher virus titers (e.g., 2-, 3-, 5-, 10-, 20-, 25-, 50-, 100-, 250-, 500-, or 1000-fold higher titers) than cells cultivated in a cell culture media other than the cell culture media described herein.

These methods may be used to produce a variety of mammalian viruses and viral vectors, including but not limited to adenoviruses, adeno-associated viruses, retroviruses and the like, and are most preferably used to produce adenoviruses or adeno-associated viruses. Following cultivation of the infected cells in the culture media described herien, the used culture media comprising viruses, viral vectors, viral particles or components thereof (proteins and/or nucleic acids (DNA and/or RNA)) may be used for a variety of purposes, including vaccine production, production of viral vectors for use in cell transfection or gene therapy, infection of animals or cell cultures, study of viral proteins and/or nucleic acids and the like. Alternatively, viruses, viral vectors, viral particles or components thereof may optionally be isolated from the used culture medium according to techniques for protein and/or nucleic acid isolation that will be familiar to one of ordinary skill in the art.

Recombinant Protein Production

The present culture media may also be used in methods for the production of recombinant proteins from cells, including eukaryotic cells grown in suspension, but preferably mammalian cells, and particularly from mammalian cells grown in suspension. Methods of producing a polypeptide according to the disclosure comprise cultivating a cell (e.g., a mammalian cell) that has been genetically engineered to produce a polypeptide in the culture media described herein under conditions suitable for expression of the polypeptide by the cell. Optimal methods for genetically engineering a mammalian cell to express a polypeptide of interest are well-known in the art and will therefore be familiar to one of ordinary skill Cells may be genetically engineered prior to cultivation in the media of the disclosure, or they may be transfected with one or more exogenous nucleic acid molecules after being placed into culture in the media. Genetically engineered cells may be cultivated in the present culture media either as monolayer cultures, or more preferably as suspension cultures according to the methods described above. Following cultivation of the cells, the polypeptide of interest may optionally be purified from the cells and/or the used culture medium according to techniques of protein isolation that will be familiar to one of ordinary skill in the art.

EXAMPLES

Example 1

Protocols for Making Microsuspensions and/or Nanosuspensions

Provided herein is a method of preparing a micro or nano suspension comprising media components. This method may, for example, allow for concentrating a medium and/or supplement way beyond solubility by microsuspension (ms) and/or nanosuspension (ns) of certain components, and further, by encapsulation of the microsuspension (ms) and/or nanosuspension (ns) to form beads, followed by desiccation of the encapsulated beads, further increase in concentration of the components occur.

To Make Microsuspensions (see FIG. 1)

For making microsuspensions of media components at ~7× concentration (without sodium phosphate):

1) Weigh 30 g of dry format powdered media, supplement or feed, without sodium phosphate, into a mortar.
2) Add 7.5 ml WFI (water for injection).
3) Using a green plastic pliable spatula, mix until the powder is wetted and begins to "take up" the water and form a paste. Thoroughly rapidly mix the paste for homogeneity, which is the microsuspension.
4) Add 1 ml of additional WFI to the microsuspensions and mix thoroughly.
5) Collect the microsuspensions into a container and use a spatula to "squeegee" the last amount of microsuspensions into a container for delivery. Volume will be ~29 ml.
6) For delivery, use a piston-delivery device (for e.g.; a syringe-type device).

Example 2

Microsuspensions and Nanosuspensions in Alginate Microcapsules

Microencapsulation can provide a mechanism of physically separating or sequestering labile components, particularly from reactive components in powdered cell culture media. By way of example, alginate or any other encapsulating matrix or capsular material can be used for microencapsulation.

Protocol for Making Encapsulated Microsuspensions

For making encapsulated microsuspensions, which is a way of further concentrating media, supplement or feed:

1) Make a microsuspension of the media, supplement or feed without sodium phosphate (for example, as described above).
2) Add 13.5 ml of 6% alginate into the microsuspension and mix thoroughly with a spatula to blend in the alginate. Volume should equal ~40.5 ml.
3) Cut parafilm circles to cover the bottoms of 4-sided (medium) polypropylene disposable weigh boats. Place parafilm into weigh boat bottom.
4) Prepare Eppendorf Repeater-Plus tips by nipping off with scizzors ~1/64" of end making sure that the cut is not as far as the location of the end of plunger when fully depressed.
5) Using Eppendorf Repeater-Plus with 2.5 ml syringe set at position 1 (25 µl), slowly pull microsuspension up into syringe. Make sure that air is not aspirated into the syringe as this would remain in the viscous microsuspension and alter volume delivered.
6) Depress the Eppendorf lever several times to prime syringe. After the microsuspension flows out of the syringe end, wipe off the end of syringe. Then hold syringe end vertically a few mm from parafilm surface, depress lever and keep at the same spot for ~5 seconds to allow all the 25 µl drop to be delivered to the parafilm surface. Then move to an adjacent position and repeat. Continue to place droplets over the entire surface of the parafilm. The alginate-microsuspension droplet will form a convex, spherical shape after sitting for a few seconds on the parafilm.
7) To cross-link the alginate and form a hydrogel, deliver 25 ml of a 133 g/L solution of calcium chloride (anhydrous) into the weigh boat. It may be necessary to hold the parafilm (and alginate-microsuspension droplets) underneath the calcium chloride solution surface using tweezers since the droplet will try to float, if the Ca solution gets underneath.
8) Hold the parafilm and alginate-microsuspension droplets under the calcium chloride for 30 seconds. Forms a bead.
9) After 30 seconds, use tweezers to grab one end of the parafilm and jostle to loosen and dislodge all the beads. It helps to turn the parafilm upside down in the weigh boat and swish back and forth in the calcium chloride. The beads will readily come off the parafilm.
10) Pass through steps 11-18 without delay since microsuspensions will be slowly dissolving throughout processing until placed onto absorbent tissue paper (Step 16).

11) Immediately fold the weigh boat in half and pour off the calcium chloride solution, being careful to hold the beads within the weigh boat by the narrowed end.
12) Relax hold on the weigh boat and immediately add (pour) enough WFI to half fill.
13) Immediately fold weigh boat as before and pour off WFI.
14) Relax hold on the weigh boat and immediately pour in enough WFI to half fill.
15) Immediately fold weigh boat as before and pour off WFI.
16) Flip over and dump each weigh boat onto double tissue paper to absorb as much water as possible from the beads.
17) Hold tissue paper over the weigh boat and scoop beads in using plastic white flexible spatula.
18) Using 2 white plastic spatulas, separate beads so that they do not touch each other.
19) Place under fume hood overnight.
20) Next morning, place beads into vacuum drying chamber over $CaSO_4$.
21) Let dry for 3 days, then remove and dislodge beads from surface of weigh boat where they will have a slight attachment. Turn a clean weigh pan upside down and use to cover the beads in their weigh pan. Lifting one end up slightly, push a white flexible spatula across the surface of the weigh pan to dislodge beads. After all are dislodged, place in the new weigh pan and put back into vacuum drying chamber over $CaSO_4$ for 4 additional days to assure dryness.

Example 3

Encapsulation of Minor Media Components Such as Vitamins

If the encapsulation targets are minor media components such as vitamins, Step 1 involves mixing a concentrate solution of the component to be encapsulated directly into a 2% alginate solution. The solution is concentrated enough so that it requires 1% or less of the volume of the 2% alginate. No formation of microsuspensions are required. This alginate-component solution is then added as 25 µl drops falling directly into 133 g/L $CaCl_2$ solution and held for 30 seconds.
  a) Drain beads of the $CaCl_2$ solution and rinse rapidly 2×.
  b) Separate the beads and dry on a flat surface for several days to ensure moisture of <1%.
  c) Then place in vacuum desiccators over CaSO4 for several days until beads are refractile and hard.
  d) Dry beads are ready for further use.

Using dried beads was like adding almost 100% nutrient supplement chemical to the bioreactor.

Example 4

Protocol for Applying Extended-Release Coating onto Alginate-Encapsulated Microsuspensions Since no access to bead coating equipment was available, a surrogate process was developed. It was found necessary to make sure absolutely no holes or weak areas would occur in the extended-release coating layer of the bead. Intact beads could not be repeatedly coated uniformly due to the nature of the organic phase being added by hand. Therefore a slide surrogate coating and testing assay was developed.

1) Make alginate-microsuspension as described above.
2) Using an Eppendorf pipettor, dot 5 µl of the alginate-microsuspension within the clear glass circular areas of the red ringed slide.
3) Immediately use a plastic spatula or other flexible tool to "smoosh" or flatten the 5 µl alginate-microsuspension to fill as much of the circular glass clear area as possible (goal is to lower the surface of the alginate-microsuspension as low as possible to assist the subsequent PLGA coating: tall beads do NOT work as they project upwards too high on the slide).
4) Place slide into 133 g/L calcium chloride solution for ~20-30 seconds.
5) Rinse by immersing in WFI.
6) Drain WFI off of slide (touch tissue to each well to suck up excess water) and dry overnight in a fume hood.
7) Then place into vacuum over CaSO4 to desiccate.
8) PLGA stock at 25 mg/0.6 ml of chloroform. Add 50 µL PLGA in chloroform to cover the well in the red ringed slide. The 50 µL volume will "fill" the circular well area and bead up to give a concave hump over the well. This volume of PLGA-chloroform will readily evaporate to form a flat, contact-lens-like covering over the dried alginate-microsuspension. Delay: 3 coats>2 coats>1 coat.
9) After the PLGA has dried, use to perform extended-release comparisons with varying concentrations and glycolic to lactic ratios.

Obtaining a uniform coating of a solution like PLGA onto a dried bead was a challenge. Several attempts were made using a variety of protocols. The protocol that worked is presented above, which was adapted from protocols till the desired coating level was obtained. For instance, flattening the bead provided the best coating results for the extended release use. Several parameters like coating component concentration, bead size, % alginate, protocols for coating, drying conditions and level of dryness, solvents for pre-coating, etc. had to be optimized in order to achieve the best results.

Example 5

Extended-Release Comparisons of Varying PLGA Concentrations and Glycolic to Lactic Ratios: Assay 1. Place 55 ml of PBS into a 50 ml centrifuge tube.
2. Add one slide of the same PLGA composition that covers all the 14 wells. Incubate horizontally at room temperature.
3. An exemplary encapsulated glucose bead was assay for glucose, to study the extended-release properties of varying ratios of the coating material components: glycolic to lactic ratios.
4. For sampling at various times, we performed the Sigma Glucose Oxidase Assay (GAGO) for glucose:
  a) 0.10 ml sample from the 50 ml centrifuge tube into a 10×75 mm glass tube or a 1.5 ml Wheaton glass rubber stoppered chemical analytical vial.
  b) 0.20 ml of Reagent into the same tube, mix.
  c) Incubate 15 min. at 37 C.
  d) Add 0.20 ml 12N sulfuric acid, mix.
  e) Controls: dilute a 1 g/L glucose solution 1:10 (0.1 ml+0.9 ml WFI, equals 100 ug/ml); serial 2× dilutions (0.5 ml glucose+0.5 ml WFI) down to 12.5 ug/ml. Controls are 100, 50, 25 and 12.5 ug/ml glucose. Also include a WFI blank.
  f) As a guide, when all of the microsuspension from all of the 14 wells is dissolved, sample needs to be diluted 1:4 to be within range of control standards. [Total glucose applied should be 0.022 g per slide at 14 wells, pg 69 NB 1138].

To read the output, use SpectraMax 384: 350 µl of samples in a 96 well tray. Either clear or dark walled work the same, no difference. Read at 540 nm absorbance.

Calculations: [from Sigma Glucose (GO) Assay Kit, Product Code GAGO-20]

$$\text{mg Glucose} = (\Delta A@540 \text{ of Test})(\text{mg Glucose in standard*})$$

*Concentration of closest standard of the 4 dilutions.
Δ means the difference between the OD reading of the test or standard minus the reading of the blank.
**Multiply the mg Glucose determined above by the dilution factor made in the sample preparation.

Example 6

Porous Metal Cylinder

A porous metal cylinder was filled with dried beads of alginate-encapsulated microsuspensions and placed within a 1 L beaker with a stir bar to simulate conditions inside a bioreactor. There was no PLGA coating of the beads for delayed-release. The graph in FIG. 11 shows that stirring within the bioreactor alone is enough to get the nutrient supplements from the beads, and to dissolve and pass into the "bioreactor". The porous metal cylinder needs no pumping, tubing, etc. to get the supplement to go into the cell culture. In fact, it is so fast that in one test experiment, the supplement in alginate beads alone (no PLGA coating) completely liberates its load within about 20 hours. Extended-release requires PLGA coating even when beads are within the porous metal. The lower chart of FIG. 11 shows that AGT powder alone can pass through the porous metal cylinder relatively quickly, but AGT alone would not work for delayed-release. A point to note is that the porous metal cylinder can be autoclaved attached to the bioreactor, and the supplement beads can be added at anytime during the culture.

FIG. 11 shows two ways that extended-release microcapsules could be used for nutrient supplementation of bioreactors. 1) Sterile microcapsules could be added directly to the bioreactor where they release components in a time-release manner (right), or 2) they may be added to a porous metal cylinder with 0.22µ pore size, keeping the beads away from contacting the cells in culture. With option 1, the beads may interfere with filtration, or may reduce cell count or productivity. With option 2, bioreactor stirring alone is enough to dissolve nutrient supplement from inside the porous metal cage and to pass into the bioreactor.

Some Exemplary Embodiments

A method of making a media, feed or supplement composition, the method comprising:
  adding a minimal volume of an aqueous solution to a dry powder of the media, feed or supplement to make a paste;
  mixing the paste vigorously to prepare a microsuspension.

A method of preparing a media composition comprising:
  preparing a microsuspension of the media according to claim 1;
  optionally, mixing in an effective amount of an anti-oxidant with the microsuspension to form a mixture;
  encapsulating the microsuspension, or the mixture of step 2, in a suitable capsular material such that a microcapsule or bead is formed;
  drying the microcapsule or bead,
  wherein the media comprises a labile substance.

The method of claim 2, wherein the labile substance is attached to a dendrimer.

The method of claim 2, wherein the media is prepared for one or more of the properties selected from the group consisting of: at least one component is in super concentration, for increased stability, for increased resistance to radiation exposure, for thermostability, for extended shelf-life and for extended release of the labile component.

The method of claim 2, wherein the media composition is assayed for assays selected from the group consisting of assay for extended-release of encapsulated components, assay for thermostability, assay for reduction of viral numbers, assay for functionality after irradiation, assay for extended shelf-life, assay for stability during transport and assay for storage at ambient temperatures.

The method of claim 2, wherein the capsular material is selected from the group consisting of alginate, poly-L-lactic acid, chitosan, agarose, gelatin, hyaluronic acid, chondroitin sulfate, dextran, dextran sulfate, heparin, heparin sulfate, heparan sulfate, gellan gum, xanthan gum, guar gum, water soluble cellulose derivatives and carrageenan.

The method of claim 2, wherein the bead if further coated with a coating that extends the release of the labile component from the bead.

The method of claim 5, wherein the coating is selected from the group consisting of poly-glycolic acid, PLGA (poly-lactic-co-glycolic acid), collagen, polyhydroxy-alkanoates (PHA), poly-ε-caprolactone, poly-ortho esters, poly-anhydrides, poly-phosphazenes, poly-amino acids, polydimethylsiloxane, polyurethranes, poly-tetrafluoroethylene, polyethylene, polysulphone, poly-methyl methacrylate, poly-2-hydroxyethylmethacrylate, polyamides, polypropylene, poly-vinyl chloride, polystyrene and poly-vinyl pyrrolidone.

The method of claim 2, wherein the bead is irradiated.

The method of claim 8, wherein the bead is assayed for sterility.

The method of claim 4, wherein the bead is irradiated with gamma-irradiation.

The method of claim 5, wherein the bead is additionally irradiated with UV rays.

The method of claim 5, wherein the bead is free of PPV and MMV viruses.

The method of claim 1 or 2, wherein the composition is a dry-format media.

The method of claim 1 or 2, wherein the labile component is selected from the group consisting of a polyamine, a growth factor, a cytokine and a vitamin.

The method of claim 2, wherein the capsular material is soluble upon reconstitution with an aqueous solvent.

The method of claim 3, wherein the encapsulating matrix encapsulates a dendrimer-labile component complex.

The method of claim 14, wherein the dendrimer is a polyamidoamine dendrimer, a polypropylenimine dendrimer, or a polypropylamine (POPAM) dendrimer.

The method of any one of claims 1-15, wherein the composition comprises a powdered cell culture medium comprising one or more amino acids.

A medium, feed or supplement composition comprising a microsuspension comprising a component.

A medium, feed or supplement composition comprising a mixture of a labile component and an anti-oxidant that is microencapsulated with a capsular matrix into a bead.

The medium, feed or supplement composition of claim 18, wherein the capsular material that is selected from the group consisting of alginate, poly-L-lactic acid, chitosan, agarose, gelatin, hyaluronic acid, chondroitin sulfate, dextran, dextran sulfate, heparin, heparin sulfate, heparan sulfate, gellan gum, xanthan gum, guar gum, water soluble cellulose derivatives and carrageenan.

The medium, feed or supplement composition of claim 18, wherein the bead is coated with a coating solution.

The medium, feed or supplement composition of claim 20, wherein the coating solution is selected form the group consisting of poly-glycolic acid, PLGA (poly-lactic-co-glycolic acid), collagen, polyhydroxyalkanoates (PHA), poly-ϵ-caprolactone, poly-ortho esters, poly-anhydrides, poly-phosphazenes, poly-amino acids, polydimethylsiloxane, polyurethranes, poly-tetrafluoroethylene, polyethylene, polysulphone, poly-methyl methacrylate, poly-2-hydroxyethylmethacrylate, polyamides, polypropylene, poly-vinyl chloride, polystyrene, poly-vinyl pyrrolidone, poly-L-lysine and polyornithine.

The medium, feed or supplement composition of claim 18, wherein the composition further comprises chelated reactive species.

The medium, feed or supplement composition of claim 21, wherein the reactive species are either cations, metals ions or trace elements.

The medium, feed or supplement composition of claim 21, wherein the chelating moieties are selelcted from the group consisting of EDTA, citrate, succinate, cyclodextrin, clatharates, dendrimers and amino acids.

The medium, feed or supplement composition of any of claims 17-23, wherein the composition is irradiated.

The medium, feed or supplement composition of claim 24 wherein the irradiation is with gamma-rays.

The medium, feed or supplement composition of claim 25, wherein the gamma-rays are 25-100 kGy.

The medium, feed or supplement composition of claim 26, wherein the gamma-rays are 30-50 kGy.

The medium, feed or supplement composition of claim 26, wherein the gamma-ray is 30 kGy.

The medium, feed or supplement composition of any of 17-28 which is added aseptically into a bioreactor.

The medium, feed or supplement composition of any of 17-29, wherein the cell culture medium, feed or supplement is protein free.

The medium, feed or supplement composition of any of 17-30, wherein the powdered cell culture medium used for the microsuspension is AGT (advanced granulation technology cell culture medium).

A use of any of the compositions described above to produce a dry format cell culture medium.

A use of any of the compositions described above to increase the shelf life of the cell culture medium.

A use of any of the compositions described above to store and handle at ambient temperatures.

Unless otherwise defined, all technical and scientific terms used herein have the same meaning as commonly understood by one of ordinary skill in the art. In case of conflict, the present specification, including definitions, will control. It will be readily apparent to one of ordinary skill in the relevant arts that other suitable modifications and adaptations to the methods and applications described herein are obvious and may be made without departing from the scope of the disclosure or any embodiment thereof. In addition, the materials, methods, and examples are illustrative only and not intended to be limiting. All patents, patent applications, and published references cited herein are hereby incorporated by reference in their entirety.

What is claimed is:

1. A method of making a eukaryotic cell culture medium, feed or supplement composition comprising a protected and stable labile component, the method comprising:
   (i) adding a minimal volume of an aqueous solution to a dry powder format of a medium, feed or supplement comprising a labile component to make a paste;
   (ii) mixing the paste vigorously to prepare a microsuspension;
   (iii) optionally, adding an effective amount of an antioxidant to the microsuspension to form a mixture;
   (iv) encapsulating the microsuspension of (ii), or the mixture of (iii), in a capsular material to form a bead; and
   (v) drying the bead to form the composition containing said protected and stable labile component.

2. The method of claim 1, wherein the bead is added aseptically into a bioreactor.

3. The method of claim 1, wherein the cell culture medium, feed or supplement composition is protein free.

4. (Examiner Amendment) The method of claim 1, wherein the powder of step (i) used for preparing the microsuspension is in an AGT (advanced granulation technology cell culture medium) format.

5. A medium, feed or supplement composition comprising a protected and stable labile component and prepared as a microsuspension by:
   (i) adding a minimal volume of an aqueous solution to a dry powder format of a medium, feed or supplement comprising a labile component to make a paste;
   (ii) mixing the paste vigorously to prepare the microsuspension;
   (iii) encapsulating the microsuspension in a capsular material to form a bead; and
   (iv) drying the bead to form the composition containing said protected and stable labile component.

6. The medium, feed or supplement composition of claim 5, further comprising an anti-oxidant within the bead.

7. The medium, feed or supplement composition of claim 6, wherein the bead is made of a capsular material that is selected from the group consisting of alginate, poly-L-lactic acid, chitosan, agarose, gelatin, hyaluronic acid, chondroitin sulfate, dextran, dextran sulfate, heparin, heparin sulfate, heparan sulfate, gellan gum, xanthan gum, guar gum, water soluble cellulose derivatives and carrageenan.

8. The medium, feed or supplement composition of claim 7, wherein the bead is coated with a coating solution.

9. The medium, feed or supplement composition of claim 8, wherein the coating solution is selected from the group consisting of poly-glycolic acid, PLGA (poly-lactic-co-glycolic acid), collagen, polyhydroxyalkanoates (PHA), poly-e-caprolactone, poly-ortho esters, poly-anhydrides, poly- phosphazenes, poly-amino acids, polydimethylsiloxane, polyurethranes, poly-tetrafluoroethylene, polyethylene, polysulphone, poly-methyl methacrylate, poly-2-hydroxyethylmethacrylate, polyamides, polypropylene, poly-vinyl chloride, polystyrene, poly-vinyl pyrrolidone, poly-L-lysine and polyornithine.

10. The medium, feed or supplement composition of claim 8, further comprising a reactive species that is chelated using a chelator.

11. The medium, feed or supplement composition of claim 10, wherein the reactive species is a cation, a metal ion or a trace element.

12. The medium, feed or supplement composition of claim 10, wherein the chelator is selected from the group consisting of EDTA, citrate, succinate, cyclodextrin, clatharates, dendrimers and amino acids.

13. The medium, feed or supplement composition of claim 5, wherein the medium, feed or supplement composition is irradiated.

14. The medium, feed or supplement composition of claim 13, wherein the irradiation is with gamma-rays.

15. The medium, feed or supplement composition of claim 14, wherein the gamma-rays are 25-100 kGy.

16. The medium, feed or supplement composition of claim 14, wherein the gamma-rays are 30-50 kGy.

17. The medium, feed or supplement composition of claim 16, wherein the gamma-ray is 30 kGy.

18. A process for increasing the shelf life of a medium, feed or supplement composition comprising a protected and stable labile component, the process comprising:
  (i) adding a minimal volume of an aqueous solution to a dry powder format of a medium, feed or supplement comprising a labile component to make a paste;
  (ii) mixing the paste vigorously to prepare a microsuspension;
  (iii) optionally, adding an effective amount of an antioxidant to the microsuspension to form a mixture;
  (iv) encapsulating the microsuspension of (ii), or the mixture of (iii), in a capsular material to form a bead; and
  (v) drying the bead to form the composition containing said protected and stable labile component to provide for the medium, feed or supplement composition at an ambient temperature.

19. The process of claim 18, wherein the bead further comprises a molecule selected from the group consisting of vitamins, amino acids, peptides, macromolecules, hormones and growth factors.

20. The process of claim 19, wherein the microsuspension of step (iv) concentrates the molecule within the bead.

* * * * *